United States Patent [19]
Kan

[11] Patent Number: 5,147,282
[45] Date of Patent: Sep. 15, 1992

[54] IRRADIATION LOADING APPARATUS

[76] Inventor: William Kan, 2000 Baker Trace, Dothan, Ala. 36303

[21] Appl. No.: 595,708

[22] Filed: Oct. 9, 1990

Related U.S. Application Data

[63] Continuation-in-part of Ser. No. 347,020, May 4, 1989, abandoned.

[51] Int. Cl.⁵ .............................................. A61N 5/00
[52] U.S. Cl. ........................................... 600/1; 600/3; 600/7; 250/496.1
[58] Field of Search .................... 600/1, 3, 5, 6, 7; 250/486.1, 497.1

[56] References Cited

U.S. PATENT DOCUMENTS

| | | | |
|---|---|---|---|
| 2,750,517 | 6/1956 | Baum | 250/497.1 |
| 2,798,164 | 7/1957 | Untermyer | 250/497.1 |
| 2,862,108 | 11/1958 | Meilink | 250/497.1 |
| 3,665,187 | 5/1972 | Stein | 250/496.1 |
| 3,669,093 | 6/1972 | Sauerwein et al. | 600/7 |
| 4,211,928 | 7/1980 | Parsons et al. | 600/1 |
| 4,220,864 | 9/1980 | Sauerwein et al. | 250/497.1 |
| 4,851,694 | 7/1989 | Rague et al. | 250/497.1 |
| 4,897,076 | 1/1990 | Puthawala et al. | 250/497.1 |

FOREIGN PATENT DOCUMENTS

| | | | |
|---|---|---|---|
| 0152124 | 8/1985 | European Pat. Off. | 600/7 |
| 3442762 | 6/1986 | Fed. Rep. of Germany | 600/7 |
| 3643902 | 12/1986 | Fed. Rep. of Germany | 250/497.1 |

Primary Examiner—Kyle L. Howell
Assistant Examiner—Robert L. Nasser, Jr.
Attorney, Agent, or Firm—Fleit, Jacobson, Cohn, Price, Holman & Stern

[57] ABSTRACT

A manual irradiation loading apparatus and method of irradiating a localized area of a human or animal patient using the manual irradiation loading apparatus. The irradiation loading apparatus comprises a radiation shielding material having at least one cable-receiving passage therethrough and a cable having a radiation source provided on one end thereof received in the cable-receiving passage. The irradiation loading apparatus is also provided with a catheter-receiving passage for joining a catheter positioned in a catheterized patient to the cable-receiving passage to permit the end portion of the cable having the radiation source thereon to be advanced into the catheterized patient for radiation treatment. In one embodiment, the irradiation loading apparatus includes a main shielding body and a removable, interchangeable cartridge to permit the irradiation loading apparatus to be used with different radiation sources.

13 Claims, 14 Drawing Sheets

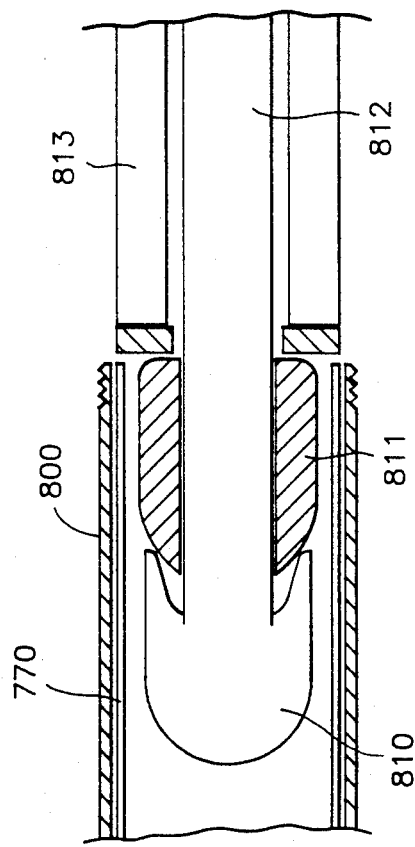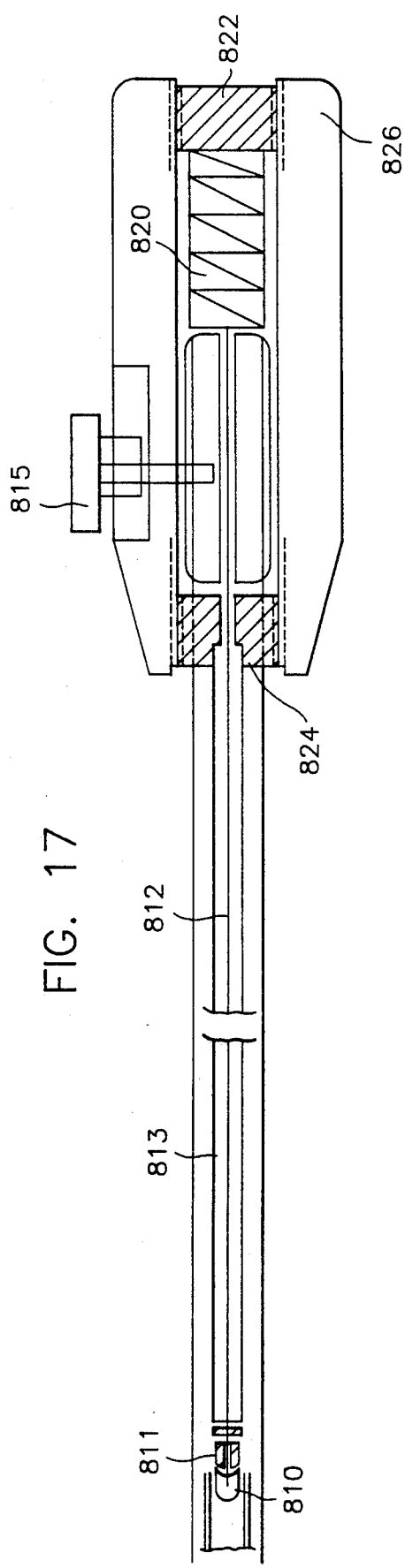

IRRADIATION LOADING APPARATUS

CROSS-REFERENCE TO RELATED APPLICATIONS

This application is a continuation-in-part of U.S. application Ser. No. 07/347,020, filed May 4, 1989.

BACKGROUND OF THE INVENTION

1. Field of the Invention

The present invention relates to an irradiation loading apparatus and to a method of irradiating a localized area using the inventive irradiation loading apparatus. The inventive irradiation loading apparatus is particularly suitable for the intrabronchial irradiation of a human patient 2. Description of Related Art Fully automated remote control machines for treating human or animal patients by local irradiation at a high dose rate from a radioactive substance are known, for example, from U.S. Pat. No. 3,669,093 to Sauerwein at el. Such automated irradiation machines suffer from a number of significant disadvantages which have prohibited their widespread use.

Most significantly, fully automated remote control irradiation machines are extremely expensive to manufacture, maintain and operate. For example, a fully automated irradiation machine, such as that disclosed in U.S. Pat. No. 3,669,093, requires an initial expenditure of between about $300,000 and $500,000 and the annual maintenance and operating cost of such an automated machine is approximately $100,000.00. The cost of purchasing, operating and maintaining such an automated irradiation machine is so prohibitive that only large urban medical centers are capable of acquiring this automated irradiation machinery and thus patients in need of localized irradiation treatment have extremely limited access thereto.

In addition, the automated irradiation machines are completely immobile and must be used in a shielded lead room. The radiation exposure level surrounding the automated irradiation machine when it is in use is extremely high and the operator of the automated machine cannot be in the room in which the machine is being used to treat a patient.

Finally, the automated irradiation machines are complex and contain a number of complex moving parts that are susceptible to breakdown and cannot be actually observed by an operator while the automated irradiation machine is in operation. For example, the automated machine moves a radioactive source of 5 to 10 curies continually over lesions or areas to be treated, thus increasing the potential for unobserved breakdown.

A typical dose rate of radiation with the automated machine is between 500 and 1000 rads/minute. This high radiation dose rate level means that the potential exposure of operating personnel would be extremely high if operating personnel were to be present in the same room as the automated irradiation machine. Thus, a lead shielded room in which the operator cannot be present is necessary in order to use the automated irradiation machine to treat a patient.

Therefore, it is object of the present invention to provide an irradiation loading apparatus which does not suffer from the disadvantages of known irradiation machines.

It is further an object of the present invention to provide a simple, inexpensive and manually operated irradiation loading apparatus which would enable smaller medical centers to provide localized irradiation treatment to patients in need thereof.

It is yet another object of the present invention to provide an irradiation loading apparatus which is portable and can be transported to and operated in a patient's hospital room, utilizing portable shields.

It is still another object of the present invention to provide an irradiation loading apparatus which can be operated by an operator in the same room with portable shields and does not require operation in a specially designed or constructed shielded room.

Yet another object of the present invention is to provide an irradiation loading apparatus which supplies low dose rate radiation to a lesion of a patient resulting in normal tissue repair at a faster rate than that for high does rate irradiation.

Additional advantages and objects of the present invention will be apparent from the accompanying description and drawings wherein:

BRIEF DESCRIPTION OF THE DRAWINGS

FIG. 17 is a cross-sectional view of a loading and retrieving cable assembly for use in the irradiation loading apparatus of FIGS. 11-13.

SUMMARY OF THE INVENTION

The present invention relates to an irradiation loading apparatus and to a method of irradiating a localized area of a human or animal patient using the inventive irradiation loading apparatus. The inventive irradiation apparatus comprises a lead or equivalent radiation shielding material body having at least one substantially longitudinally extending cable-receiving passage therein. A cable having radioactive seeds or a similar radioactive source provided on one end thereof or a radioactive wire or cable is received in the longitudinally extending cable-receiving passage. During storage of the inventive irradiation loading apparatus, the portion of the cable bearing the radioactive source material is located in the cable-receiving passage within the shielding material body. During use, a catheter positioned in a catheterized patient is joined to the shielding material body and the portion of the cable bearing the radioactive source material is advanced through the cable-receiving passage in the shielding material body and into the catheter.

In a first embodiment of the present invention, the inventive irradiation loading apparatus comprises a lead or equivalent shielding material body having an axial passage formed therethrough. The axial passage comprises two co-axial portions of different diameters. One of the co-axial portions is a cable-receiving passage and the other of the co-axial portions is a catheter-receiving passage. The cable-receiving passage and the catheter-receiving passage meet at an interface substantially centrally located within the shielding material body. Preferably, the cable-receiving passage comprises a fine gauge tubing surrounded by the shielding material body and the catheter-receiving passage comprises a passage formed directly in the shielding material body. In accordance with the other embodiments of the present invention, the inventive irradiation loading apparatus comprises a housing, two end plates provided at opposite ends of the housing, one or more longitudinally extending passages defined by fine gauge tubing extending between the two end plates such that one of the ends of the tubing is received in a passage formed in one end plate and the opposite end of the tubing is received in a passage formed in the opposite end plate, and a lead or equivalent shielding material surrounding the passage(s) formed by the tubing and substantially filling the volume defined between the housing and the two end plates. In accordance with this embodiment of the present invention, one of the end plates is provided with a passage or passage having two coaxial portions to provide an interface between the cable-receiving tubing and a larger catheter-receiving passage.

DETAILED DESCRIPTION OF THE PREFERRED EMBODIMENTS

Figure 1:
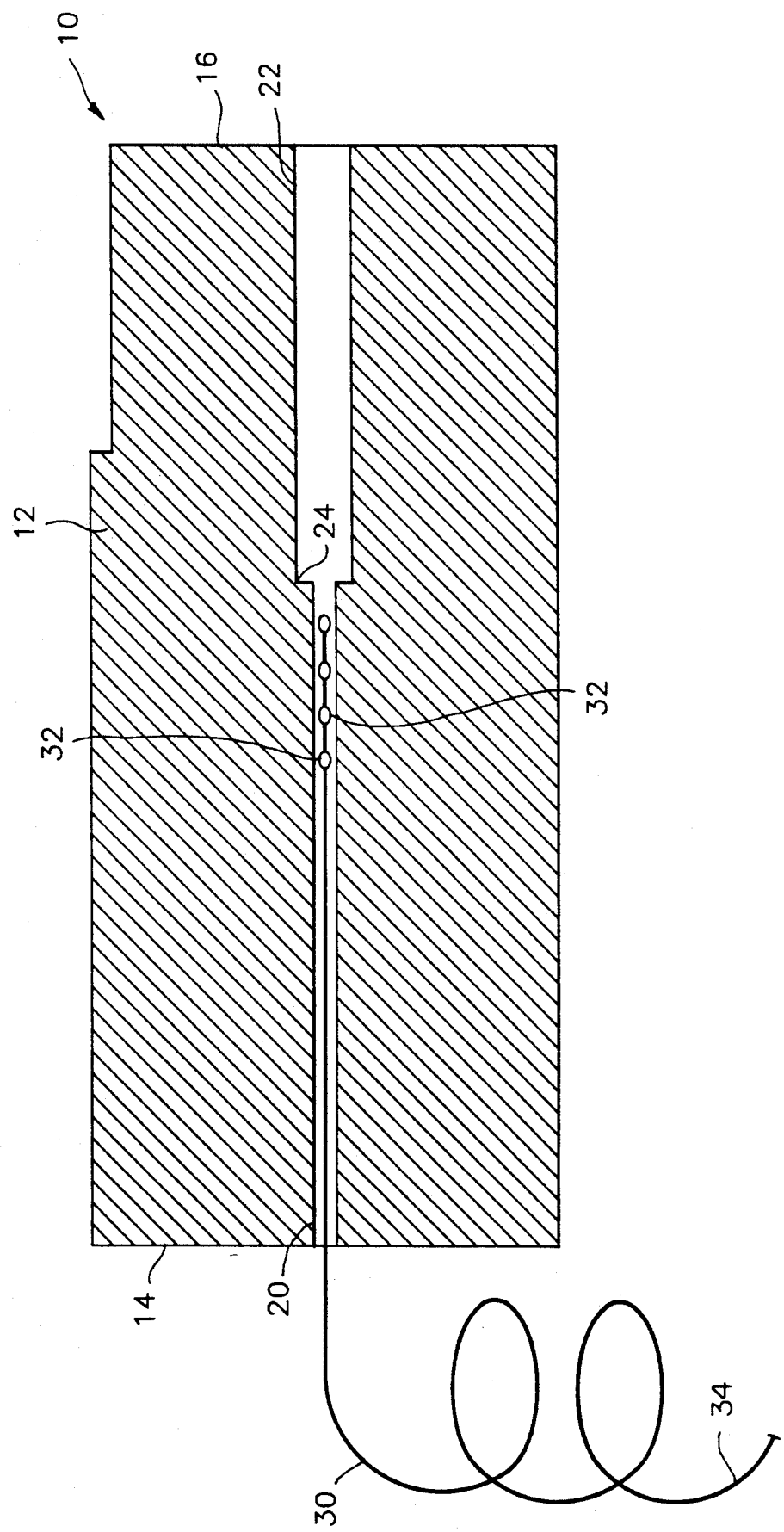
FIG. 1 is a longitudinal cross-sectional view of a first embodiment of the invention.

Referring to FIG. 1, there is shown a longitudinal cross-sectional view of a first embodiment of the present invention. The irradiation loading apparatus 10 illustrated in FIG. 1 comprises a shielding material body 12 made of lead or an equivalent radiation shielding material. The body 12 has an axial passage formed therethrough extending from a first end 14 of the body 12 to the opposite end 16 of the body 12. The passage in the body 12 has two co-axial portions 20, 22. The first portion 20 of the passage is a cable-receiving passage. The second portion 22 of the passage is a catheter-receiving passage and has a larger diameter than the cable-receiving passage 20. The cable-receiving passage 20 and the catheter-receiving passage 22 meet at an interface 24 which is substantially centrally located in the body 12. Preferably, the cable-receiving passage 20 has a fine gauge, hollow tubing positioned therein and the catheter-receiving passage 22 is preferably defined by the shielding material body 12, i.e., no additional tubing or the like is provided in the catheter-receiving passage 24.

A cable 30 having radioactive seeds 32 or a similar source of radiation provided on one end portion thereof is slidably and removably received in the cable-receiving passage 22 of the body 12. The opposite end portion 34 of the cable 30 extends outside the body 12 for easy access and manual feeding of the cable, as explained hereafter.

Figure 5:
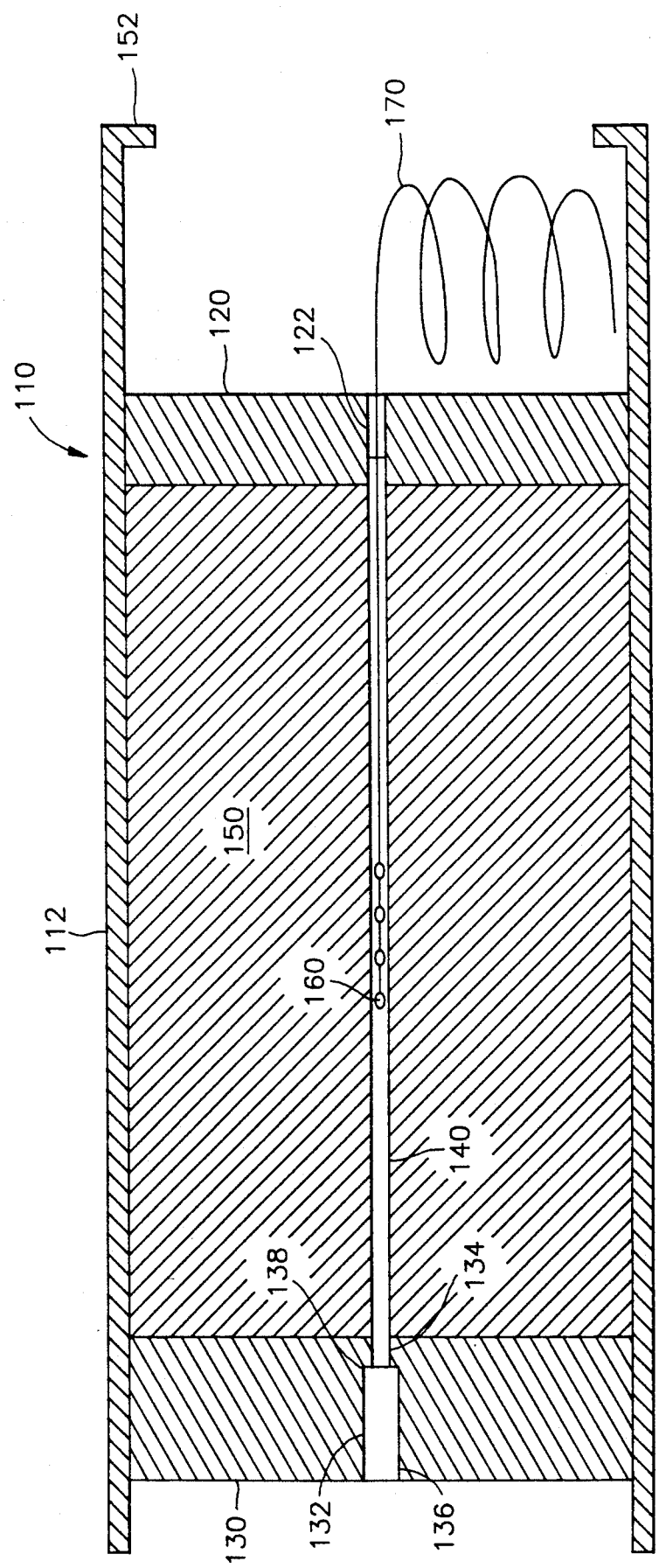
FIG. 5 is a longitudinal cross-sectional view of a second embodiment of the present invention.

A second embodiment of the invention irradiation loading apparatus is illustrated in FIG. 5. This irradiation loading apparatus 110 comprises a housing 112 and two end plates 120, 130. A cable-receiving passage is formed by tubing 140, which extends from end plates 120 to end plate 130. End plate 120 has a passage 122 formed therethrough in which one end of the tubing 140 is received. End plate 130 has a passage 132 formed therethrough which passage has two co-axial portions, a tubing-receiving portion 134 and a catheter-receiving portion 136. The catheter-receiving portion 136 of passage 132 has a larger diameter than the tubing-receiving portion 134, and the catheter-receiving portion 136 and tubing-receiving portion 134 meet at interface 138. Lead or an equivalent shielding material 150 surrounds the tubing 140 and fills the volume defined between the end plates 120, 130 and the housing 112. Preferably, the housing 112, the end plates, 120, 130 and the tubing 140 are made of stainless steel or an equivalent material.

As illustrated in FIG. 5, the housing 112 preferably extends beyond the end plate 120 and terminates in a flanges 152 which extends radially inwardly from the housing 112. The space defined by the flange 152 and the end plate 120 forms a convenient storage space for the cable 170 which extends outside the cable-receiving passage formed by tubing 140, when the end of the cable 170 bearing the radioactive source material 160 is located in the storage position as shown in FIG. 5. The cable 170 is of the same type as cable 30 described with reference to FIG. 1.

Figure 6:
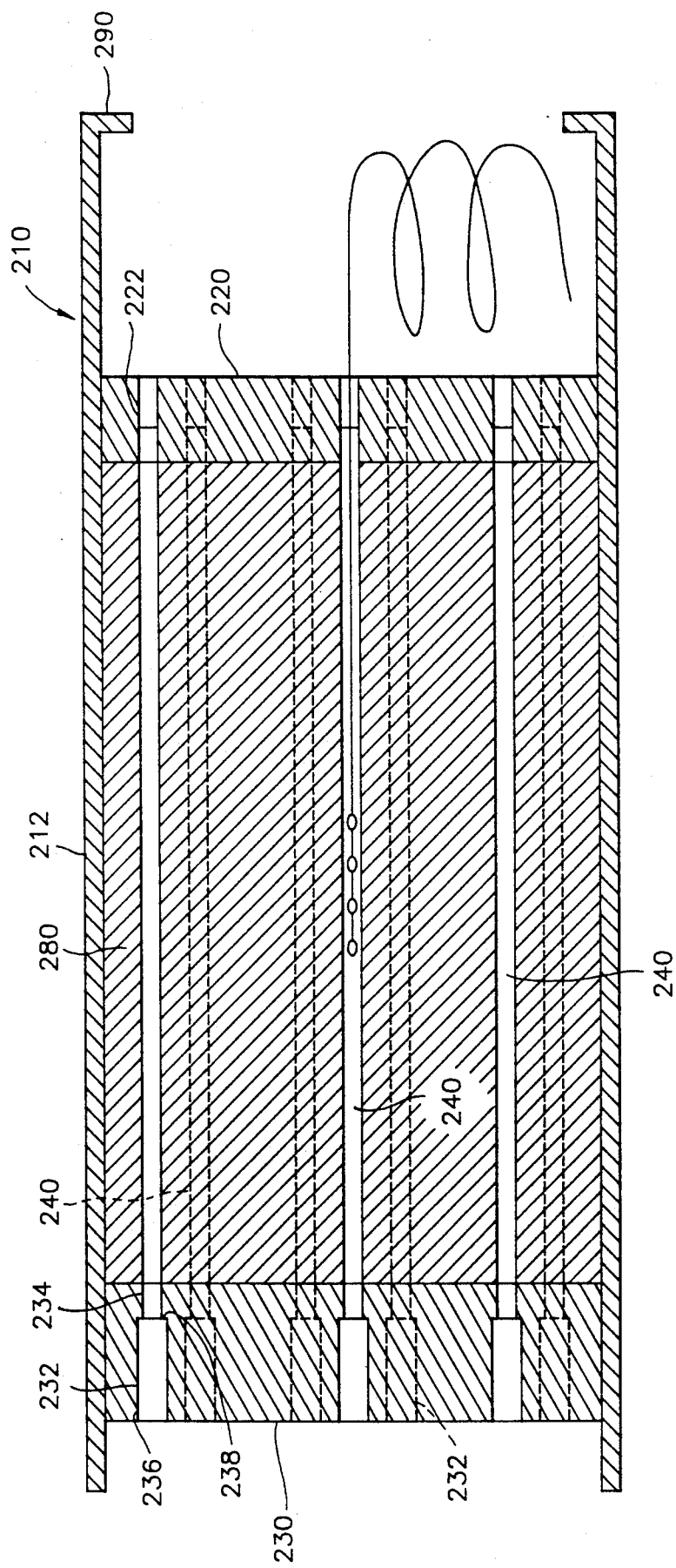
FIG. 6 is a longitudinal cross-sectional view of a third embodiment of the present invention.

FIG. 6 is a longitudinal cross-sectional view of a third embodiment of the inventive irradiation loading apparatus. This irradiation loading apparatus 210 is similar to that shown in FIG. 5 and comprises a housing 212 and two end plates 220, 230. This embodiment of the irradiation loading apparatus comprises a plurality of cable-receiving passages formed by tubing 240. Tubing 240 extends from end plate 220 to end plate 230. End plate 220 has a plurality of passages 222, with individual ends of the tubing 240 being received in each passage 222. End plate 230 has a plurality of passages 232 formed therethrough, which passages have two co-axial portions, a tube-receiving portion 234 and a catheter-receiving portion 236. The catheter-receiving portion 236 of each passage 232 has a larger diameter than the tubing-receiving portion 234. Each catheter-receiving portion 236 and tubing-receiving portion 234 meet at an interface 238. As in the embodiment shown in FIG. 5, lead or an equivalent radiation shielding material 280 surrounds the tubing 240 and fills the volume defined by the end plates 220, 230 and the housing 212. Again, preferably the housing 212, the end plates 220, 230 and the tubing 240 are made of stainless steel or any equivalent material. Housing 212 preferably extends beyond the end plate 220 and has a radially inwardly extending flange 290 provided thereon.

Figure 7:
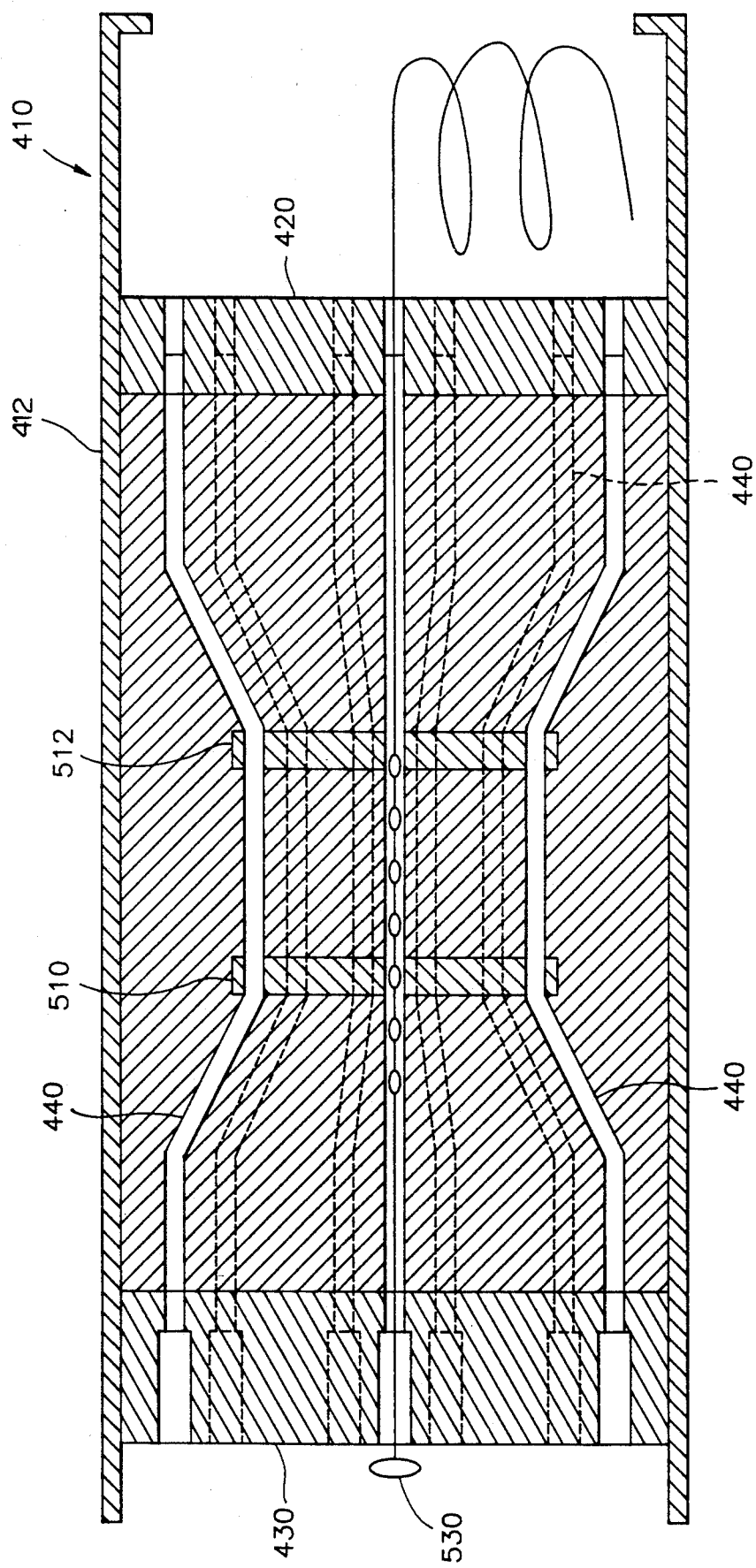
FIG. 7 is a longitudinal cross-sectional view of a fourth embodiment of the present invention.

A fourth embodiment of the inventive irradiation loading apparatus is illustrated in FIG. 7. This irradiation loading apparatus 410 comprises a housing 412, two end plates 420, 430 and a plurality cable-receiving passages formed by tubing 440, similar to the embodiment illustrated in FIG. 6. However, the fourth embodiment of the inventive irradiation loading apparatus 410 further comprises two aligned constricting rings 510, 512 through which tubing 440 passes. The constricting rings 510, 512 bend the tubing 440 radially inwardly in the central portion of the irradiation loading apparatus 410 to provide additional radiation shielding in the central portion of the irradiation loading apparatus 410. Each of the constricting rings 510, 512 has a plurality of passages formed therethrough, such that individual tubing 440 passes through an individual passage in each constricting ring 510, 512.

In the embodiments of the present invention which comprise more than one cable-receiving passage, such as the embodiments illustrated in FIGS. 6 and 7, the tubing forming the cable-receiving passages may be of varying diameters to accommodate various commercially available radioactive sources and/or radioactive wire in a single apparatus. Some of the tubing forming the cable-receiving passages may be 17 gauge tubing, for example, whereas others of the tubing may be of larger and smaller gauge as necessary or desirable. Although the embodiments shown in FIGS. 6 and 7 have a total of 12 additional cable-receiving passages therein, it is to be understood that any suitable number of passages may be provided. Similarly, although cable has been shown only in one passage in FIGS. 6 and 7, it is to be understood that cable can be simultaneously received in any number of the cable-receiving passages.

Figure 2:
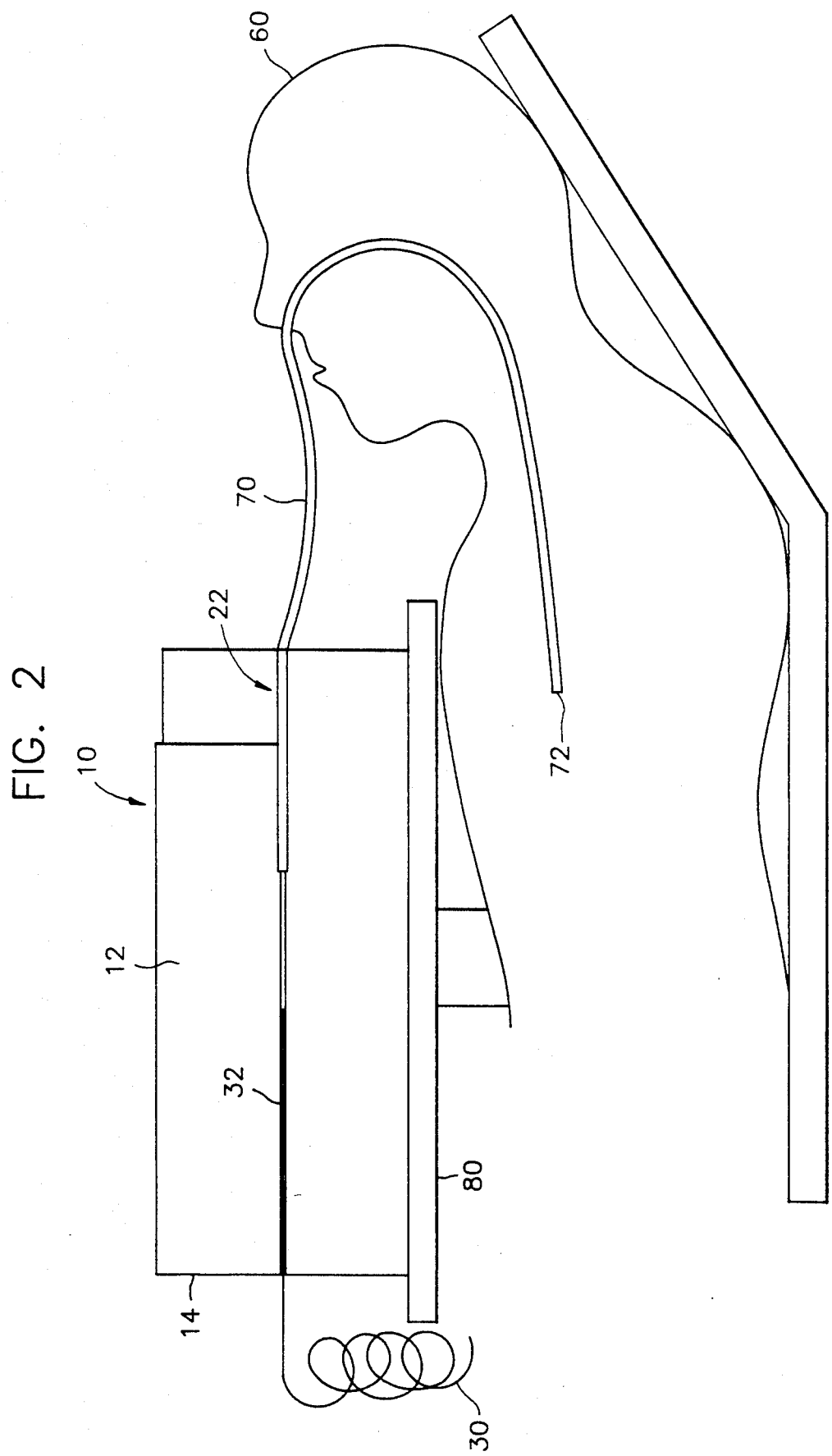
FIGS. 2, 3 and 4 illustrate the use of the first embodiment of the present invention to provide localized irradiation to a catheterized patient.
Figure 3:
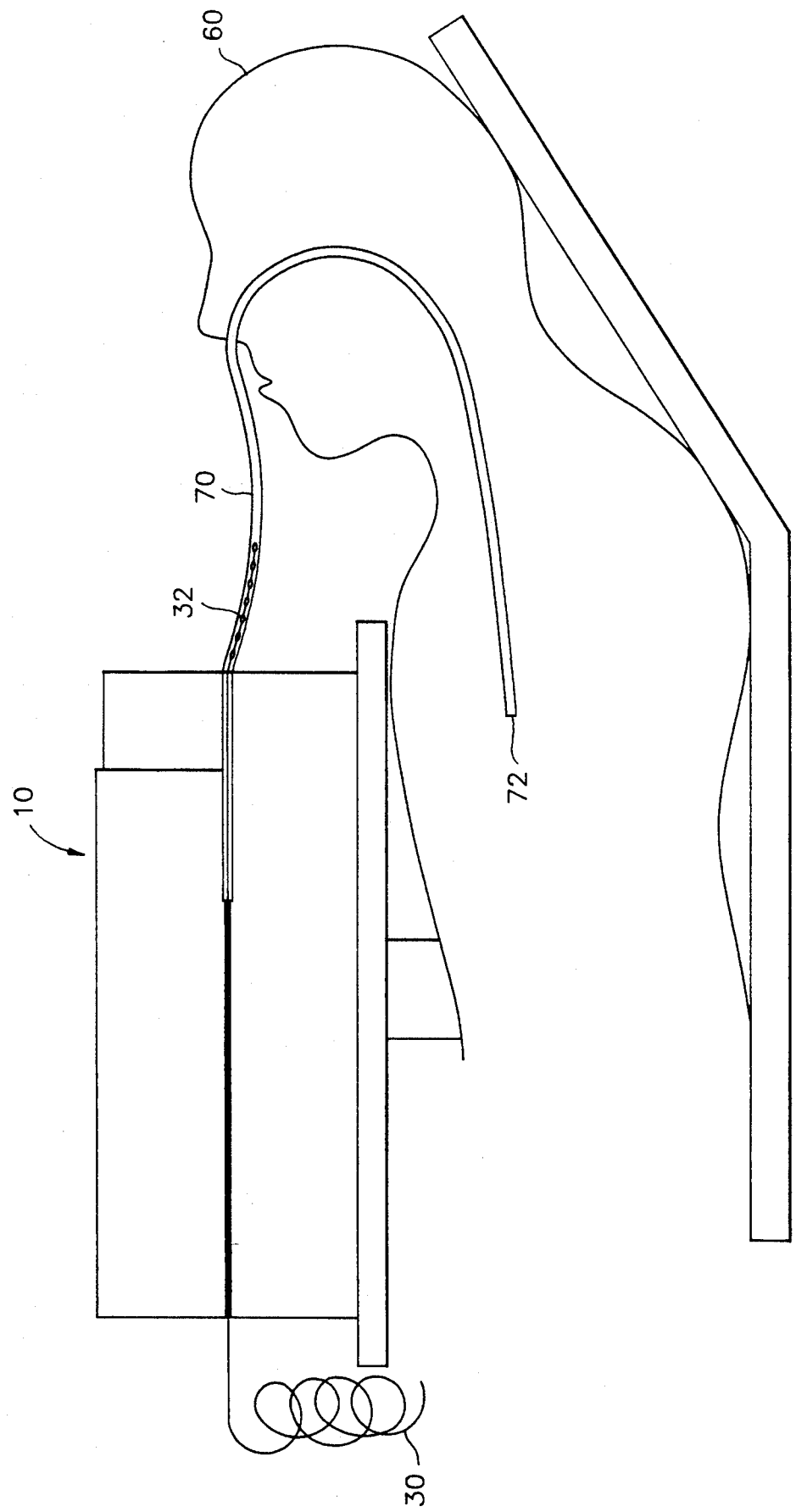
Figure 4:
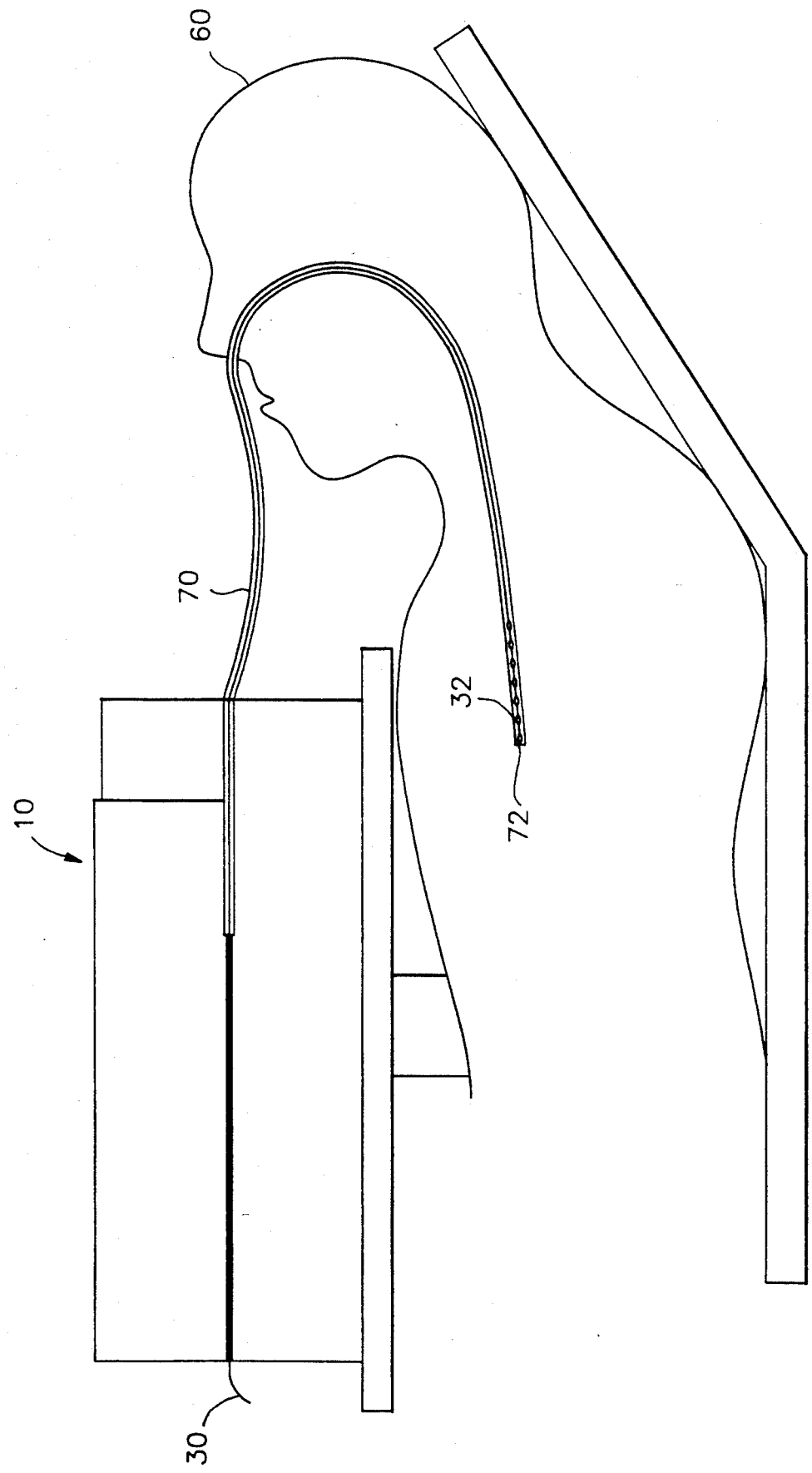

Referring now to FIGS. 2-4, there is illustrated a method of locally irradiating a patient, such as a human being or animal, for treatment purposes. Although the method illustrated in FIG. 2-4 is shown with respect to the embodiment of the present invention illustrated in FIG. 1, it is to be understood that the same method steps would be employed with the second, third and fourth embodiments of the inventive irradiation loading apparatus using the same procedures.

The method illustrated in FIG. 2-4 is a method of intrabronchial irradiation. Of course, it is to be understood that the inventive irradiation loading apparatus is also suitable for use in other types of localized irradiation treatments.

In preparation for the intrabronchial irradiation using the inventive irradiation loading apparatus 10, the patient's lesion was visually identified using a bronchoscope and the blind-end 72 of an after-loading catheter 70 was introduced through the working channel of the bronchoscope (not shown) Upon positioning the after-loading catheter 70 at the point where the radioactive source material will subsequently be located, the catheter 70 was stiffened with a plain steel cable, for easy manipulation.

Before retrieving the bronchoscope from the patient, the lesion boundary, i.e., beginning and ending locations of the lesion, were "marked" with two lead markers by taping them externally to the patient's chest. These two positions were "marked" with fluoroscopic X-ray corresponding to the visual bronchoscope location in the patient.

Viewing the patient through fluoral X-ray and keeping the after-loading catheter 70 at the same location as "marked" by the lead markers, the bronchoscope would then be retrieved steadily from the patient, leaving behind only the after-loading catheter 70 (with steel cable insert) in the patient. The catheter 70 was then marked at the nasal entrance and taped securely to the patient's nasal bridge. The patient was then transported back to his room to allow a brief recovery and await loading of radioactive Ir-192 seeds.

The irradiation loading apparatus 10 with radioactive seeds 32 in the storage position as shown in FIG. 2 was transported to the patient's room. By placing the irradiation loading apparatus 10 on a patient's adjustable dinner tray table 80, the irradiation leading apparatus 10 was positioned near the patient in a ready loading position. The steel cable insert was then removed from the after-loading catheter 70 and the catheter cut to the proper length and inserted into the catheter-receiving passage 22 in the irradiation loading apparatus 10 as shown in FIG. 2.

At this point, the patient 60 was ready for loading of the radioactive seeds 32 into the after-loading catheter 70. By feeding the cable 30 connected with all the radioactive seeds 32, such as Ir-192 seeds, from the end 14 of the irradiation loading apparatus 10, the cable 30 is quickly passed through the irradiation loading apparatus 10 into the after-loading catheter 70 as shown FIG. 3. Feeding of the steel cable 30 was continued until total stop at the blind-end 72 of the catheter 70. Due to the high activity of the radioactive Ir-192 seeds, the initial feeding should be done with a long forceps holding a portion of the after-loading catheter 70 in order to minimize radiation exposure. With practice, the cable feeding process can easily be done in 10-15 seconds.

With all the seeds 32 at the marked lesion area, the remainder the steel cable 30 was manually freed from the body 12 and the body 12 and adjustable dinner tray table 80 were temporarily removed from the patient 60. The freed cable 30 was then taped securely to the catheter and the radioactive seed were left in the patient 60 for about 2 hours. Normally, 24 seeds total and 6-7 mg eq. activity per seed with no pacing are ordered. In this manner, a surface dosage of 600-750 cGy at 1 cm radius from the linear source is provided for one treatment session. A maximum of 4 sessions are given to a patient at a specific lesion site.

After the lesion target dose was achieved, the body 12 can be used in a reverse process to retrieve the steel cable 30 with radioactive seeds 32 back to the storage position. Finally, as shown in FIG. 2, the irradiation loading device 10 can be safely transported back to a designated irradiation source storage area.

During testing of the inventive irradiation loading device, 90% of patients experienced relief of symptoms associated with an obstructive intrabronchial carcinoma. Review of the film and ring badge reports on both the radiation therapist and the radiation physicist performing these test procedures did not show an excessive radiation exposure. The inventive irradiation loading device and method of treatment have proven during testing to be simple, economical and safe for the treatment of interbronchial carcinoma.

The irradiation loading apparatus of the present invention can be simply and economically produced. The first embodiment of the inventive irradiation loading apparatus, illustrated in FIG. 1, can be easily manufactured by providing an appropriate mold and filling the mold with molten lead or molten equivalent radiation shielding material and then permitting the molten material to solidify. The longitudinal passage can be conveniently formed during the molding process by providing appropriately sized tubing or the like within the mold cavity so that the molten lead or equivalent shielding material surrounds the tubing or the like prior to solidification to form the passage having two co-axial portions.

The embodiment shown in FIG. 5-7 can be readily produced as follows. Two end plates are provided and tubing is inserted in corresponding passages provided in the end plates such that the tubing extends between the two end plates. In the embodiment shown in FIG. 7, the tubing is inserted in one end plate and then through the constricting rings and finally into the other end plate. Material for the housing is wrapped around the end plates so as to surround the tubing and enclose the volume between the two end plates. An opening is provided in the housing and molten lead or equivalent radiation shielding material is poured into the housing through the opening so as to fill the volume surrounding the tubing and defined between the housing and the two end plates. The molten lead or equivalent shielding material is then allowed to solidify and a piece of material of the same or similar composition to that of the housing is then applied over the opening in the housing. The covering for the opening may take the form of an additional support upon which the irradiation loading apparatus can rest while in use.

Subsequent to formation of the portion of the irradiation loading apparatus comprising the lead or equivalent shielding material, cable having a radiation source material, preferably in the form of seeds or the like, is then inserted into the cable-receiving passage in the irradiation loading apparatus so that the radiation source material is positioned in the storage position as discussed above. A pin 530 or other suitable stopping means as shown in FIG. 7 may be inserted through the catheter-receiving passage in the irradiation loading apparatus so as to prevent the cable from extending beyond the lead or equivalent shielding material to insure proper storage position.

Commercially available cable having radioactive seeds provided on an end portion thereof or radioactive wire is suitable for use in the inventive irradiation loading apparatus. A particularly preferred radioactive source is a cable having Ir-192 seeds provided thereon. The irradiation loading apparatus of the present invention can be used to provide an effective does rate on the order of 5.0 to 10.0 rads per min. Those having skilled in the art will be readily able to determine the appropriate does rate for various conditions requiring irradiation treatment. Since there is a vast body of clinical experience with low does rate while the same body of experience does not exist for high does rate irradiation.

The housing or body of the inventive irradiation loading apparatus may be of any convenient size; however due to the weight of lead and equivalent shielding materials, it is prefereable that the housing or body be of small dimensions to ensure portability. An especially preferred embodiment comprises a housing or body having a radius of about 5 cm with a catheter-receiving passage(s) having a diameter of about 0.21 cm and a cable-receiving passage(s) having a diameter of about 0.15 cm. Of course, the inventive irradiation loading apparatus is not limited to these dimensions or to a cylindrical shape. Of source, modifications may be made without departing from the scope of the present invention.

The embodiment depicted in FIG. 6 has application for tumors of the brain or oral cavity while the multiple channel interior of the devise as depicted in FIG. 7 has an application for tumors of the breast or esophagus. Thus the interior portion of the devise could be embodied in interchangeable cartridge form thus allowing different configurations of cable receiving passages for various types of tumors.

Figure 8:
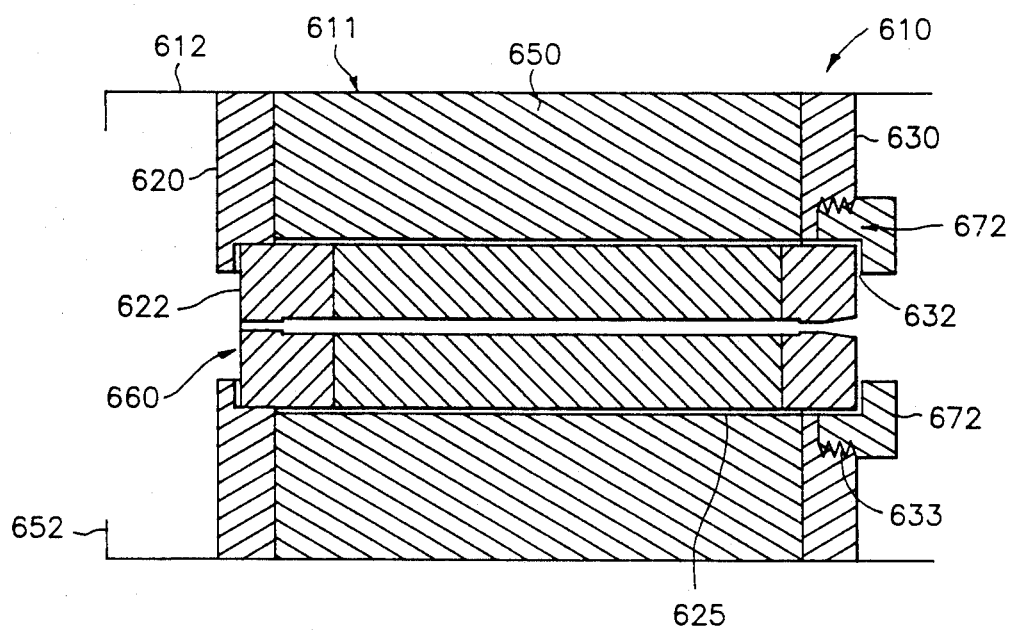
FIG. 8 is a longitudinal cross-sectional view of a fifth embodiment of the irradiation loading apparatus of the present channel, including an interchangeable single-channel cartridge.
Figure 10:
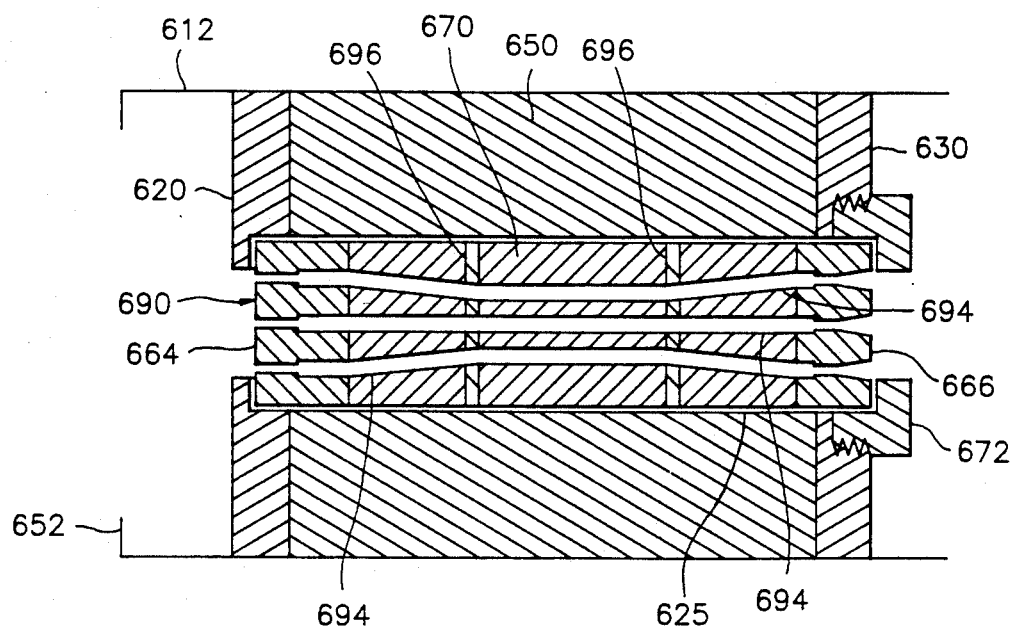
FIG. 10 is a longitudinal cross-sectional view of the fifth embodiment of the irradiation loading apparatus of the present invention, including an interchangeable multi-channel cartridge.
Figure 11:
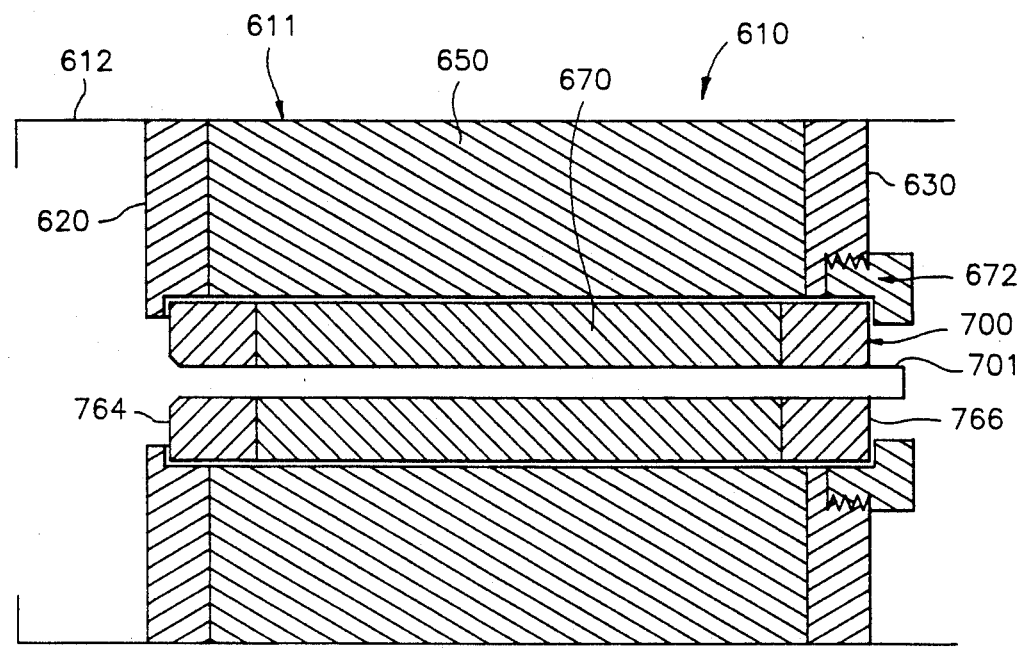
FIG. 11 is a longitudinal cross-sectional view of the fifth embodiment of the irradiation loading apparatus of the present invention, including a gynecologic cartridge.

The manual portable irradiation loading apparatus was further modified into cartridge form with a hollow cylinder as the main shielding body to hold interchangeable cartridges as shown in FIGS. 8, 10 and 11. Individual cartridges were made to accommodate specific commercially available and commonly used radioactive sources (dimensions and appearance listed in Table 1).

TABLE 1

Commonly Used, Commercially Available Radioactive Sources for Radiation Therapy Utilized in Specific Interchangeable Cartridges of the Loading Apparatus.

| RADIATION SOURCE | PHYSICAL FORM | EXTERNAL DIMENSIONS | APPLICATION/ PROCEDURES |
|---|---|---|---|
| IRIDIUM | Seeds in Ribbon | O.D.* = 0.5 mm | General Interstitial Bronchial |
| Ir-192 | | L** = 3.0 mm | Esophagus |
| IODINE | Seeds | O.D. = 0.8 mm | Stereotactic Brian |
| I-125 | | L = 4.5 mm | |
| CESIUM | Standard Tube | O.D. = 3.1 mm | Gynecological |
| Cs-137 | Sources | L = 20.0 mm | |

*O.D. = Outside Diameter
**L = Length

Figure 9:
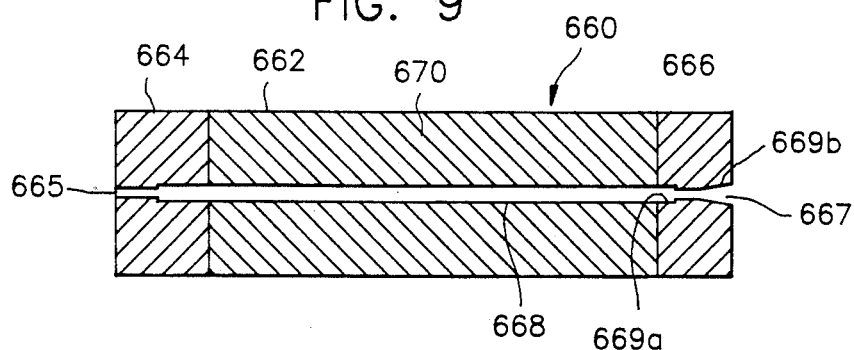
FIG. 9 is a longitudinal cross-sectional view of a single-channel cartridge useful in the fifth embodiment shown in FIG. 8.

By exchanging cartridges in the loading apparatus one can use the apparatus for a variety of procedures suing either single-channel (FIG. 9) or multi-channel (FIG. 10) cartridges. One cartridge was build exclusively for bronchial irradiation consisting of a single channel using a single strand of Ir-192 seed ribbon as shown in FIG. 9. Another cartridge similar to the bronchial cartridge contains multiple channels. The multichannel cartridge in FIG. 10 was designed to carry multiple Ir-192 seed ribbons used in esophageal irradiation and in multiple catheter interstitial procedures such as mandible, floor of the mouth, or well-defined breast lesion, etc.

Referring now to FIG. 8 there is shown a fifth embodiment of the present invention. This irradiation loading apparatus 610 comprises a main shielding body 611 including a housing 612, two end plates 620, 630 and a cylindrical inner wall 625 extending between the two end plates 620, 630. The cylindrical inner wall 625, together with portions of the two end plates 620, 630, defines a cartridge receiving passage. Lead or an equivalent radiation shielding material 650 fills the volume defined between the housing 612, the end plates 620, 630 and the inner wall 625. End plate 620 has a passage 622 extending therethrough, one portion of the passage 622 having a diameter substantially equal to the diameter of the inner wall 625 and another portion having a diameter smaller than the diameter of the inner wall 625. The smaller diameter portion of the passage 622 is formed by a radially inwardly extending edge of the end plate 620. The end plate 630 also has a passage 632 extending therethrough. One portion of the passage 632 has a diameter substantially equal to the diameter of the inner wall 625 and another portion of the passage 632 has a diameter greater than the diameter of inner wall 625. The larger diameter portion of the passage 632 is formed with threads 633 such that the end plate 630 forms a part of a screw coupling structure. The housing 612 preferably extends beyond the end plate 620 and terminates in a flange 652 which extends radially inwardly form the housing 612. The space defined by the flange 652 and the end plate 620 forms a convenient storage space for a radiation source cable (not shown), as explained with respect to FIG. 5. Preferably, the housing 612, and plates 620, 630 and inner wall 625 are made of stainless steel or an equivalent material.

The irradiation loading apparatus 610 further comprises an interchangeable, i.e., removable and replaceable, cartridge 660, shown in FIG. 9. The cartridge 660 comprises an outer cylindrical wall 662 and two end plates 664, 666. A cable receiving passage which is formed by tubing 668, such as stainless steel tubing or the like, extends from end plate 664 to end plate 666. Lead or equivalent radiation shielding material 670 surrounds the tubing 668 and fills the volume defined between end plates 664, 666 and outer cylindrical wall 662. End plate 664 has a passage 665 therethrough in which one end of the tubing 668 is received. End plate 666 has a passage 667 formed therethrough, which passage 667 has a tubing-receiving portion 669a and a catheter-receiving portion 669b. Preferably the catheter-receiving portion 669b has a funnel shape as shown in FIGS. 8 and 9.

To assemble the irradiation loading apparatus 610, the cartridge 660 is inserted into the passage defined by the inner cylindrical wall 625 of the main shielding body 611 such that end plate 664 abuts against the radially inwardly extending edge of end plate 620. Cartridge 660 is secured in the main shielding body 611 by cartridge lock-ring 672 which is provided with threads to matingly engage the threaded portion of end plate 630. The assembled irradiation loading apparatus 610, with the cartridge secured therein, is used in the same manner as described with respect to FIGS. 2-4. The irradiation loading apparatus 610 may be provided with handles as shown in FIG. 13.

The embodiment shown in FIG. 8 includes a cartridge 660 having a single channel extending therethrough. As shown in FIG. 10, the cartridge can be a multi-channel cartridge 690 having a plurality of cable-receiving passages formed by tubing 694. Any number of cable-receiving passages may be provided in cartridge 690, for examples, 13 or 25 such passages. The multi-channel cartridge 690 may include a pair of constricting rings 696 through which the tubing 694 passes. The purpose and function of the constructing rings is the same as discussed above with reference to FIG. 7.

Figure 12:
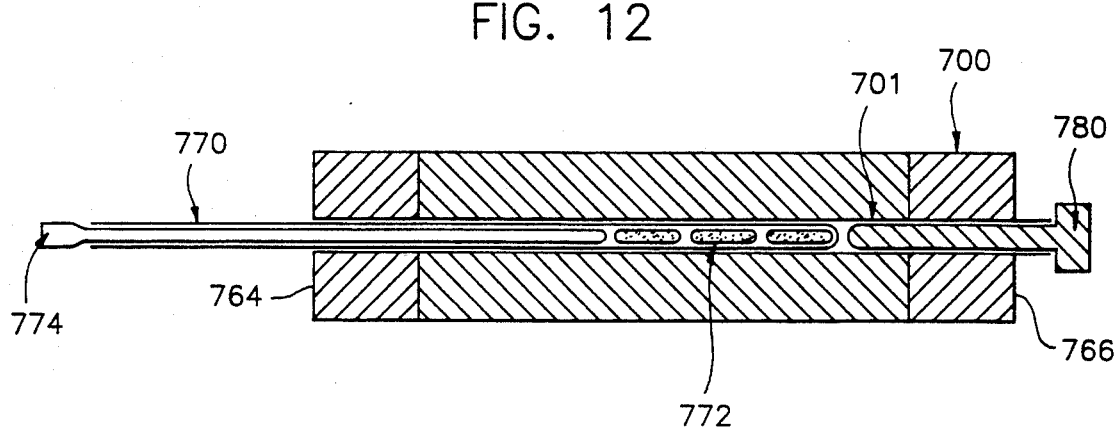
FIG. 12 is a longitudinal cross-sectional view of a loaded gynecologic cartridge useful in the irradiation loading apparatus of FIG. 11.

The cartridge used with the main shielding body 611 may be constructed to receive a radiation source other than a seeded cable. Referring now to FIGS. 11-13, another cartridge constructed for uterine/vaginal irradiation treatment is described. This gynecological cartridge 700 was constructed with a single large metallic tube 701 running centrally form end to end through cartridge 700, extending from end plate 764 and extending through and beyond end plate 766, as shown in FIG. 11 and FIG. 12. Metallic tube 701 is surrounded by lead or equivalent radiation shielding material 670. The metallic tube 701 is of an appropriate size to allow a plastic tandem 770 containing standard Cesium tube sources 772 to move freely within the cartridge 700. The plastic tandem 770, Cesium-137 standard tube source 772, and plastic stopper insert 774 are widely used commercial products. The source stopper 780 was intended to keep the closed end plastic tandem 770, containing radioactive Cesium sources, in place inside the metallic tube 701 of the cartridge 700. This is especially important when the loading apparatus 610 is turned vertically as shown in FIG. 13 during source selection and placement into the plastic tandem 770 as well as source transport to and from a patient.

Figure 13:
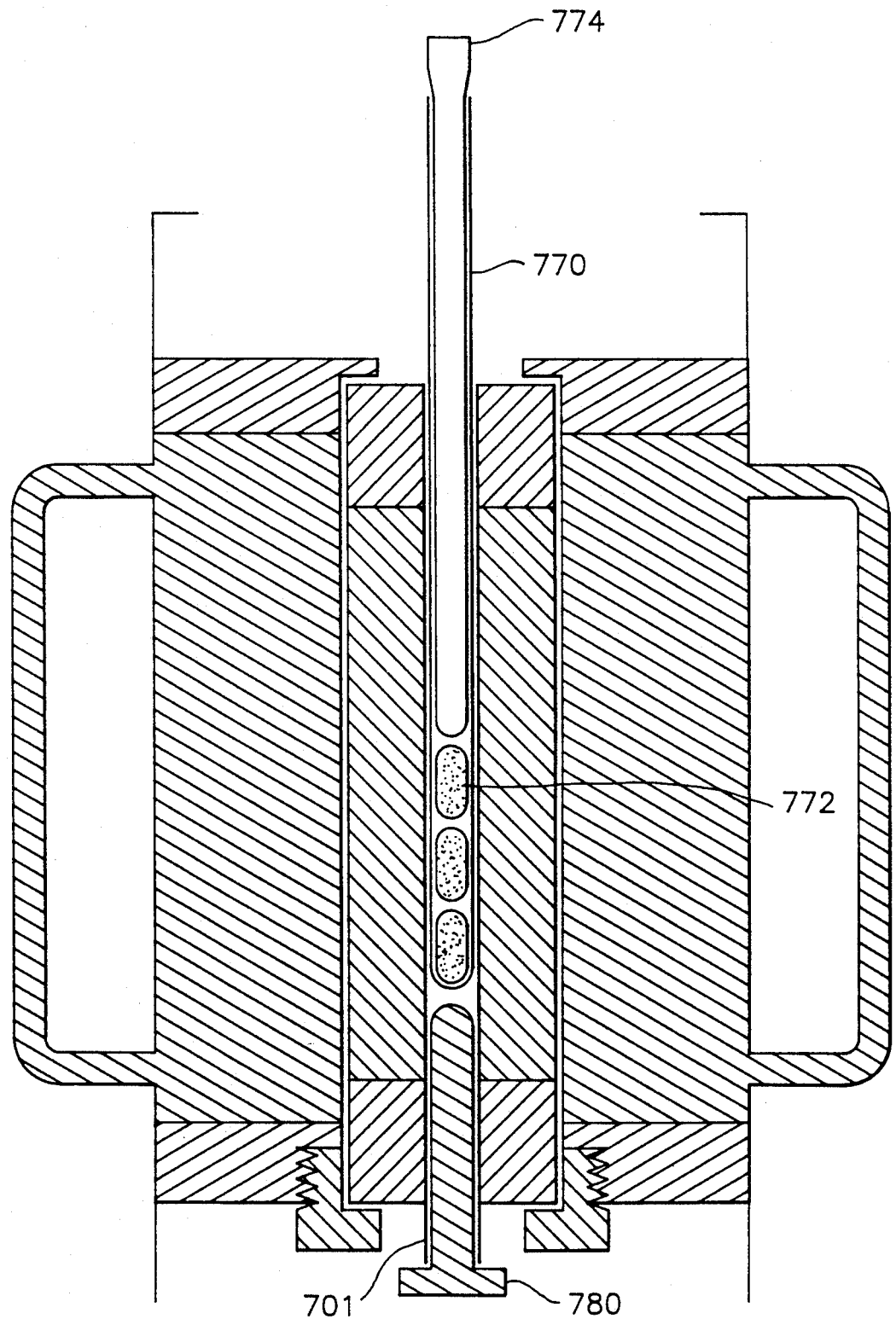
FIG. 13 is a longitudinal cross-sectional view of the irradiation loading apparatus of FIG. 11 having the loaded gynecologic cartridge of FIG. 12 positioned therein.

The source selection and placement of the radioactive source into the plastic tandem 770 with loading apparatus 610 in vertical position as in FIG. 13 must be done behind a protective lead shield and barrier, usually available in the radioactive source storage or preparation room generally referred to as the "hot" laboratory.

Figure 14:
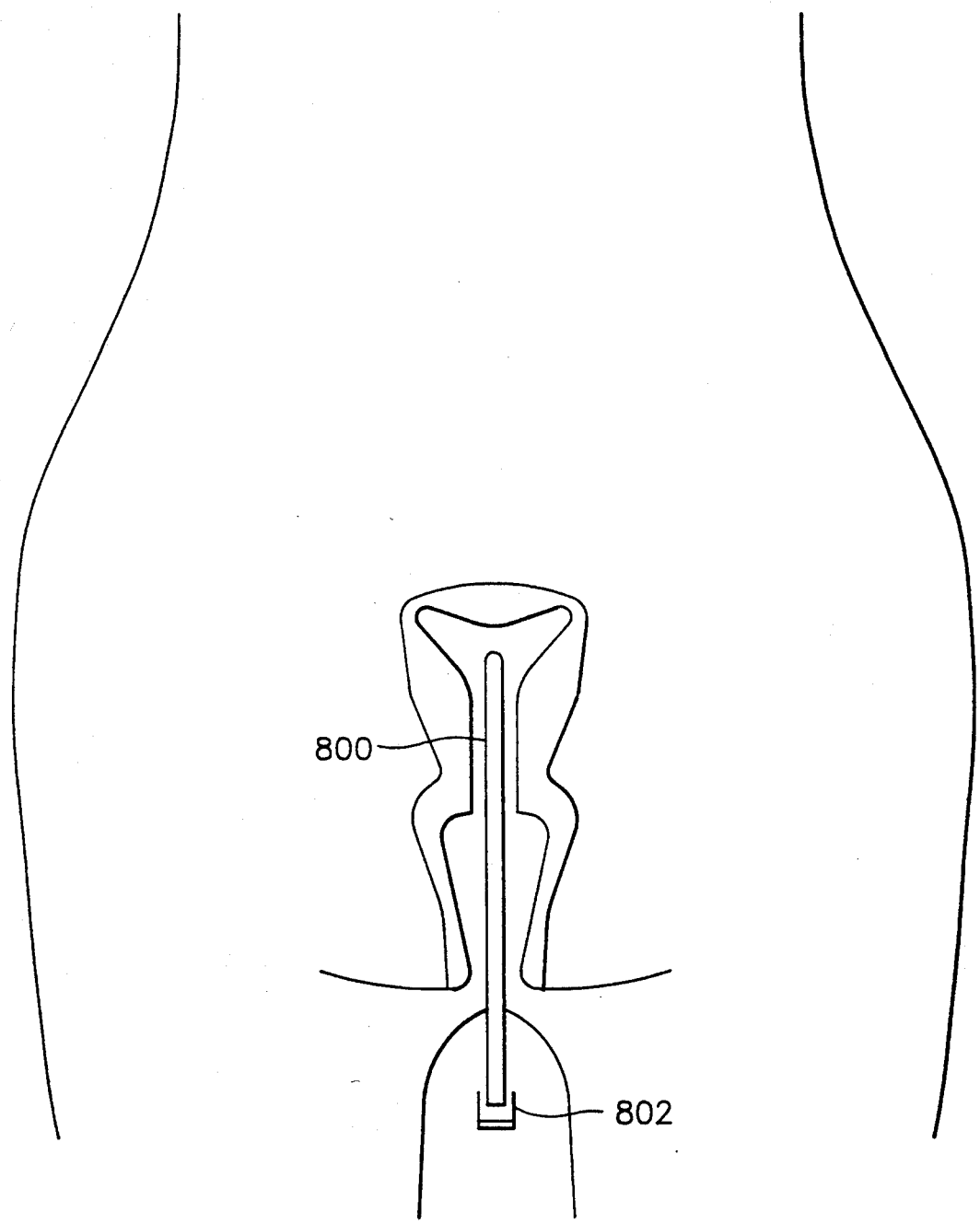
FIGS. 14 and 15 illustrate the use of the irradiation loading apparatus of FIGS. 11-13 to provide localized irradiation to a patient.

The loading apparatus 610 with Cs-137 source(s) is now ready to be transported to the patient room with negligible radiation exposure. FIG. 14 illustrates the position of any empty metal tandem 800 in the patient as placed by the radiation oncologist. The number of sources and their activities, determined through radiographs, depend on the metal tandem position in the patient and the cancerous tissue margin. The metal tandem 800 mentioned her is a widely used commercial product for uterine-cervical cancer treatment, available, for example, from 3M Products.

A special cart was constructed to transport the manual irradiation loading apparatus 610 to the patient's room in the vertical position as illustrated in FIG. 13.

Figure 15:
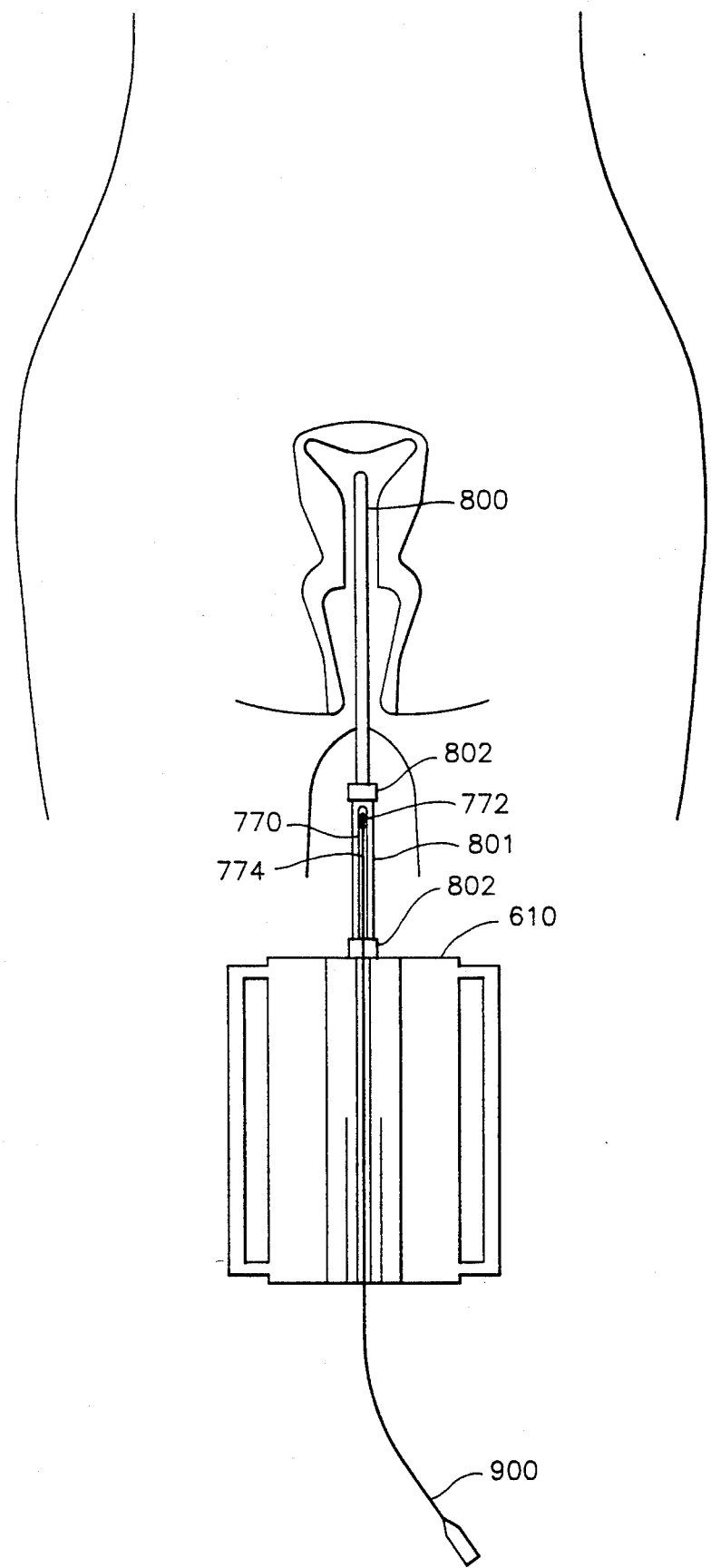
Figure 16:
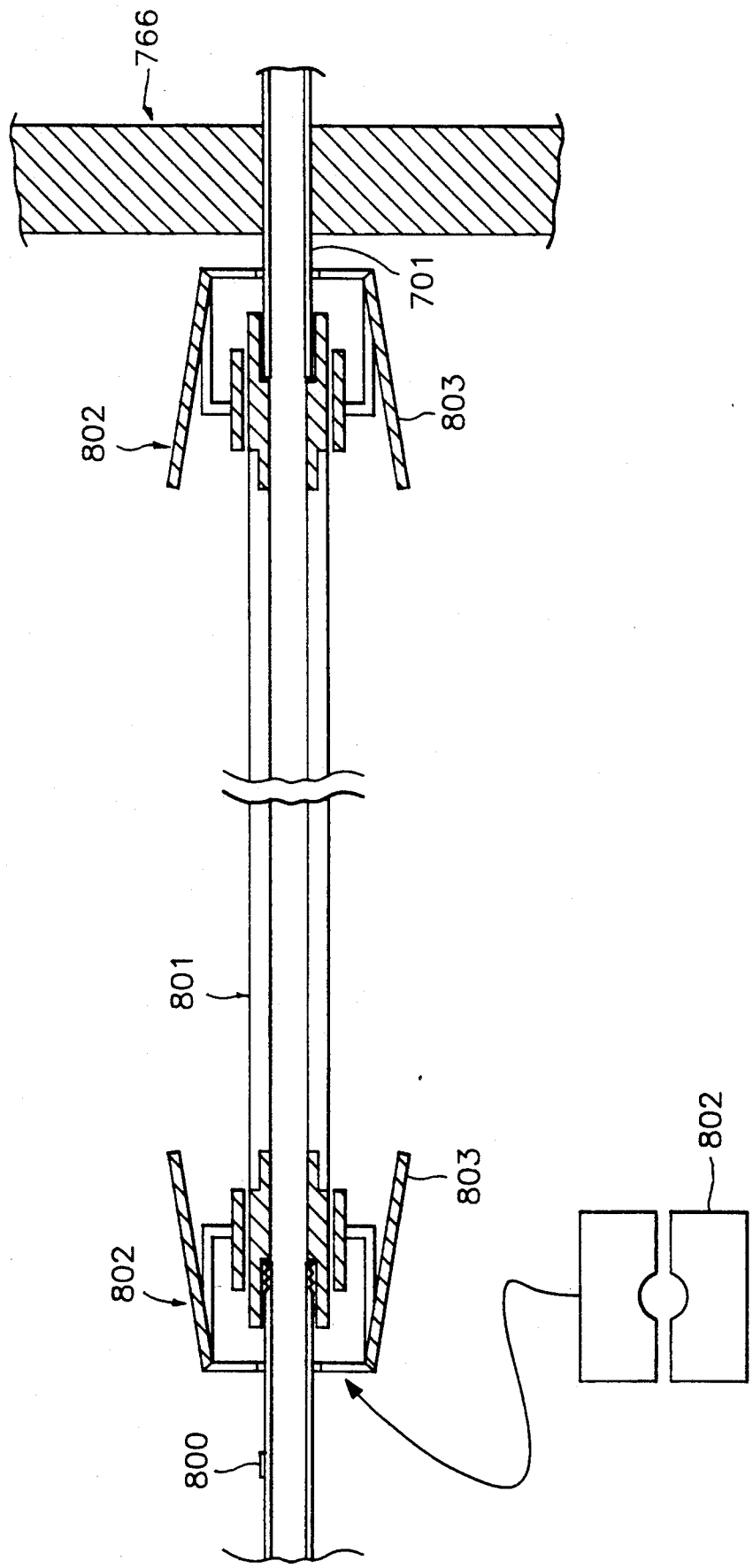
FIG. 16 is a longitudinal cross-sectional view of the means for connecting the irradiation loading apparatus to provide localized irradiation to a patient as shown in FIGS. 14 and 15.

For loading the radiation sources into the metal tandem 800 inserted in the patient, the manual loading apparatus 610 containing Cs-137 sources 772 was placed between the patient's thighs as shown in FIG. 15. The metal cap 802 in FIG. 14 of the metal tandem 800 and source stopper 780 from the loading apparatus 610 were then removed. A short semi-transparent docking tube 801 with quick release connectors 802 at both ends, as shown in FIG. 16, were than quickly attached, one end to the loading apparatus 610 and the other end to the patient's metal tandem 800. Quick release connectors 802 are of the spring clip-type having actuating levers 803. Three portable lead shields were placed around the patient's bed, usually one on each side and one at the end to further reduce unnecessary exposure. The complete connection prior to source transfer is shown in FIG. 15.

Using the loading-retrieval cable assembly 900, shown in FIG. 17, the plastic tandem 770 containing radioactive sources 772 with the plastic stopper insert 774 can be pushed rapidly through the loading apparatus 610 via the short docking tube 801 and on into the metal tandem 800. The short semi-transparent docking tube 801 allows the user a quick visual clearance check of the sources at a distance or more than 3 feet. The empty loading apparatus 610 and the detached docking tube 801 were then temporarily removed and stored nearby and the metal cap 802 again fastened back on the metal tandem 800 to keep source 772 in place during treatment.

When irradiation treatment was completed, usually 24 to 48 hours later, radioactive sources 772 were removed with a specially constructed loading and retrieving cable assembly designed for one-handed operation as shown in FIG. 17.

For source removal, the metal cap 802 and the plastic stopper insert 774 of the plastic tandem 770 were first removed from the patient. The semi-transparent docking tube 801 and the empty loading apparatus 610 were again connected as in FIG. 15. The loading and retrieving cable, comprising a steel cable 812 surrounded by a teflon tube 813, was advanced through the loading apparatus 610 and docking tube 801 and stopped at the opening of the plastic tandem 770. Only the cable tip 810 and the silicon rubber ring 811 were passed inside the plastic tandem 770.

Next, the steel cable 812 set screw 815 was triggered retracting the steel cable 812; thereby forcing the silicon rubber ring 811 to expand radially, firmly gripping the inner wall of the plastic tandem 770. This retracting mechanism includes set screw 815 with eccentric lock-up, spring return 820, plugs 822, 824 and handle 826. With the loading and retrieving cable firmly connected to the plastic tandem 770 containing the Cs-137 sources 772, one could pull the cable out pas the docking tube 801 and retrieving sources 772 back to the storage position inside the loading apparatus 610. Releasing the docking tube 801 from the apparatus 610, the source stopper 780 was then inserted back into the apparatus 610 and the loading apparatus 610 returned to the vertical position as shown in FIG. 13. The Cesium sources inside the loading apparatus could then be safely transported back to the "hot" laboratory for storage.

What is claimed is:

1. An irradiation loading apparatus, comprising:
   a main shielding body, said body having a housing, a first housing end plate and a second housing stop end plate on either end of said housing, and a cylindrical central passageway extending between said first and second housing end plates wherein said second housing stop end plate includes a passage extending therethrough, an outer portion of said second housing end plate passage having a diameter smaller than a diameter of the cylindrical central passageway and an inner portion having the diameter equal to the diameter of the cylindrical central passageway, and said first housing end plate includes a passage extending therethrough, an outer portion of said first housing end plate passage having a diameter larger than the diameter of the cylindrical central passageway and having threads to accept a lock ring screw coupling structure, and an inner portion having a diameter equal to the diameter of the cylindrical central passageway;
   an interchangeable cartridge removably placed within the cylindrical central passageway between the two housing nd plates of the main shielding body comprising:
      first and second cartridge end plates, an outer portion of said first cartridge end plate having a tapered patient catheter-receiving first passage therethrough, and an inner portion of said first cartridge end plate having a continuous first passage with a diameter equal to the smaller end of the tapered portion therethrough, and said second cartridge end plate having a second passage with a diameter equal to the smaller end of the tapered first passage of the first cartridge end plate throughout,
      an outer cylindrical cartridge wall extending between the first and second cartridge end plates, and
      a third passage formed by tubing extending between the first and second cartridge end plates, linking the first and second passages;
   a cartridge lock-ring having threads for engaging the interchangeable cartridge securely in the passage between the first and second housing end plates of the main shielding body; and
   means for carrying a radiation source being slidably and removably received in said third receiving passage such that a first portion of the carrying means having the radiation source thereon can be advanced from a storage position in the third receiving passage through the inner portion of the first receiving passage of the first cartridge end plate and into a patient catheter received in the outer portion of the first receiving passage of the first cartridge end plate, and wherein said first portion of said carrying means having said radiation source thereon is located in the third receiving passage when said irradiation loading apparatus is in a storage position, wherein a portion of the carrying means extends out of said second receiving passage beyond said second cartridge end plate.

2. An irradiation loading apparatus, as claimed in claim 1, wherein said first and second cartridge end plates of said cartridge have a plurality of first and second receiving passages, respectively, and said cartridge comprises a plurality of third receiving passages.

3. An irradiation loading apparatus as claimed in claim 2, wherein said cartridge further comprises first and second constricting rings through which the plurality of third receiving passages pass.

4. An irradiation loading apparatus as claimed in claim 1, wherein said carrying means is a cable.

5. An irradiation loading apparatus according to claim 4, wherein said main shielding body further comprises flanges extending beyond said second housing end plate and radially inwardly forming a housing for storing the cable.

6. An irradiation loading apparatus as claimed in claim 4, wherein said housing, first and second housing end plates and inner wall are made of stainless steel.

7. An irradiation loading apparatus as claimed in claim 4, wherein said irradiation source is Iridium-192 and is in the form of a seed ribbon.

8. An irradiation loading apparatus as claimed in claim 7, wherein said cartridge further comprises first and second constricting rings through which the plurality of third receiving passages pass.

9. An irradiation loading apparatus as claimed in claim 1, wherein said carrying means is a plastic tandem including a source stopper inserted in the outer portion of the first receiving passage to keep the plastic tandem in place inside the passage and having a plurality of passages within a single cartridge.

10. An irradiation loading apparatus as claimed in claim 9, wherein said radiation source is Cesium-137.

11. An irradiation loading apparatus as claim 9, wherein said housing, first and second housing end plates and inner wall are made of stainless steel.

12. An irradiation loading apparatus as claimed in claim 1, wherein the outer portion of said first cartridge catheter receiving end plate has a tapered bore.

13. An irradiation loading apparatus as claimed in claim 1, wherein said main shielding body is made of lead.

* * * * *